United States Patent
Shiodera et al.

(10) Patent No.: US 10,429,466 B2
(45) Date of Patent: Oct. 1, 2019

(54) MRI APPARATUS, IMAGE PROCESSING APPARATUS, AND IMAGE PROCESSING METHOD

(71) Applicant: TOSHIBA MEDICAL SYSTEMS CORPORATION, Otawara-Shi (JP)

(72) Inventors: Taichiro Shiodera, Ohta (JP); Tomoyuki Takeguchi, Kawasaki (JP)

(73) Assignee: Canon Medical Systems Corporation, Otawara-shi (JP)

(*) Notice: Subject to any disclaimer, the term of this patent is extended or adjusted under 35 U.S.C. 154(b) by 198 days.

(21) Appl. No.: 15/280,437

(22) Filed: Sep. 29, 2016

(65) Prior Publication Data
US 2017/0097399 A1 Apr. 6, 2017

(30) Foreign Application Priority Data
Oct. 6, 2015 (JP) ................................ 2015-198220

(51) Int. Cl.
*G01V 3/00* (2006.01)
*G01R 33/44* (2006.01)
(Continued)

(52) U.S. Cl.
CPC ............ *G01R 33/443* (2013.01); *A61B 5/055* (2013.01); *G01R 33/34* (2013.01); *G01R 33/385* (2013.01); *G01R 33/543* (2013.01); *G01R 33/546* (2013.01); *G01R 33/56* (2013.01); *G01R 33/5659* (2013.01); *G06T 7/0012* (2013.01); *A61B 2576/00* (2013.01);
(Continued)

(58) Field of Classification Search
CPC .................................................. G01R 33/443
USPC ........................................ 324/309, 307, 318
See application file for complete search history.

(56) References Cited

U.S. PATENT DOCUMENTS

2011/0234222 A1* 9/2011 Frahm ................ G01R 33/4824
324/309
2015/0084628 A1 3/2015 Sato et al.
(Continued)

FOREIGN PATENT DOCUMENTS

| JP | 2013-521013 A | 6/2013 |
| JP | 2015-62637 | 4/2015 |
| JP | 2015-062637 A | 4/2015 |

OTHER PUBLICATIONS

Tian Liu et al. "Morphology Enabled Dipole Inversion (MEDI) from a Single-Angle Acquisition: Comparison with COSMOS in Human Brain Imaging," Magnetic Resonance in Medicine 66, 2011, 7 Pages.

(Continued)

*Primary Examiner* — Louis M Arana
(74) *Attorney, Agent, or Firm* — Oblon, McClelland, Maier & Neustadt, L.L.P.

(57) ABSTRACT

According to one of embodiments, an MRI apparatus includes at least one receiving coil configured to receive magnetic resonance signals from an object; and processing circuitry configured to generate an image based on the magnetic resonance signals, calculate a weighting map of the image based on at least one of a sensitivity characteristic of the receiving coil and a distance from a magnetic field center, and generate a quantitative susceptibility image, which quantitatively indicates magnetic susceptibility inside a body, from the image by using the weighting map.

19 Claims, 13 Drawing Sheets

(51) Int. Cl.
  A61B 5/055    (2006.01)
  G01R 33/34    (2006.01)
  G01R 33/385   (2006.01)
  G01R 33/54    (2006.01)
  G06T 7/00     (2017.01)
  G01R 33/56    (2006.01)
  G01R 33/565   (2006.01)
  G01R 33/3415  (2006.01)
  G01R 33/561   (2006.01)

(52) U.S. Cl.
  CPC ...... *G01R 33/3415* (2013.01); *G01R 33/5611* (2013.01); *G01R 33/56545* (2013.01); *G06T 2207/10088* (2013.01)

(56) References Cited

U.S. PATENT DOCUMENTS

2015/0276903 A1* 10/2015 Taniguchi ............ G01R 33/243
                                              324/318

2018/0203087 A1* 7/2018 Ye .................... G01R 33/56545

OTHER PUBLICATIONS

Klaas P. Pruessmann et al. "SENSE: Sensitivity Encoding for Fast MRI," Magnetic Resonance in Medicine 42, 1999, 11 Pages.

Yi Wang et al. "Quantitative Susceptibility Mapping (QSM): Decoding MRI Data for a Tissue Magnetic Biomarker," Magnetic Resonance in Medicine 73, 2015, 20 Pages.

Tian Liu et al. "A novel background field removal method for MRI using projection onto dipole fields (PDF)," NMR Biomed, Nov. 2011, 14 Pages.

F. Schweser et al. "A Novel Approach for Separation of Background Phase in SWI Phase Data Utilizing the Harmonic Function Mean Value Property," Proceedings of the International Society Magnetic Resonance in Medicine Scientific Meeting and Exhibition 18, 2010, 1 Page.

Japanese Office Action dated Jun. 25, 2019 in Japanese Patent Application No. 2015-198220.

* cited by examiner

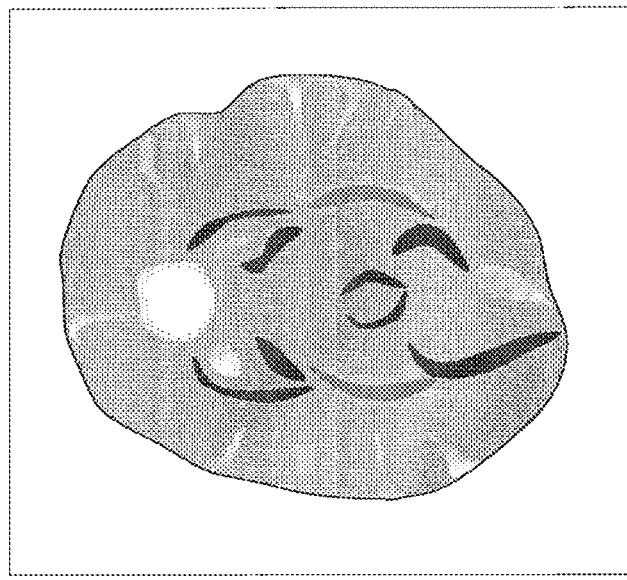
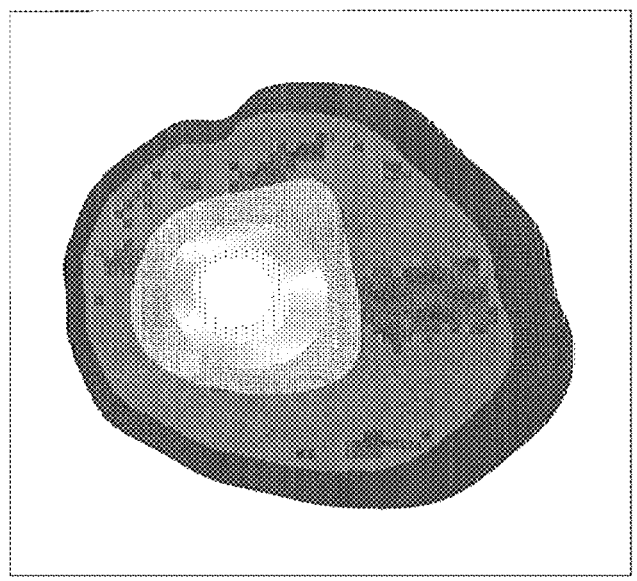
FIG. 8

US 10,429,466 B2

MRI APPARATUS, IMAGE PROCESSING APPARATUS, AND IMAGE PROCESSING METHOD

CROSS-REFERENCE TO RELATED APPLICATION

This application is based upon and claims the benefit of priority from Japanese Patent Application No. 2015-198220, filed on Oct. 6, 2015, the entire contents of which are incorporated herein by reference.

FIELD

Embodiments described herein relate generally to an MRI (Magnetic Resonance Imaging) apparatus, an image processing apparatus, and an image processing method.

BACKGROUND

QSM (Quantitative Susceptibility Mapping) is known as a technique of calculating magnetic susceptibility of each tissue from phase signals included in an image acquired by an MRI apparatus. QSM can be interpreted as one of biomarker imaging techniques in which an index of a biological condition and a specific disease condition are imaged. Mapping of magnetic susceptibility of each tissue enables diagnosis of disease related to iron and ferrugination. For example, it is said that an abnormal region in Alzheimer's disease or multiple sclerosis causes the ferrugination. Such a ferrugination region in the brain can be identified by QSM.

Additionally, since an intracerebral bleeding area and a calcified area are difficult to discriminate from each other in an image acquired by a conventional MRI apparatus, thus, a CT (Computed Tomography) apparatus has been mainly used for discriminating an intracerebral bleeding area and a calcified area from each other.

Meanwhile, it is known that magnetic susceptibility of lime becomes minus and magnetic susceptibility of blood becomes plus, when magnetic susceptibility of water is set to be zero as a reference. Thus, an intracerebral bleeding area and a calcified area can be discriminated from each other by performing QSM on an image obtained by an MRI apparatus, which has an advantage of involving no X-ray exposure over a CT apparatus.

BRIEF DESCRIPTION OF THE DRAWINGS

In the accompanying drawings:

FIG. 8 is a schematic diagram, illustrating a cerebral phase image after phase-wrapping removal (i.e., the image on the right side of FIG. 7) and a cerebral tissue phase image after background field removal processing;

DETAILED DESCRIPTION

According to one of embodiments, an MRI apparatus includes at least one receiving coil configured to receive magnetic resonance signals from an object; and processing circuitry configured to generate an image based on the magnetic resonance signals, calculate a weighting map of the image based on at least one of a sensitivity characteristic of the receiving coil and a distance from a magnetic field center, and generate a quantitative susceptibility image, which quantitatively indicates magnetic susceptibility inside a body, from the image by using the weighting map.

Hereinafter, embodiments of an MRI apparatus, an image processing device, and an image processing method will be described with reference to the accompanying drawings. In the following embodiments, components assigned with the same reference number are assumed to function in the same manner and duplicate description is omitted.

(First Embodiment)

Figure 1:
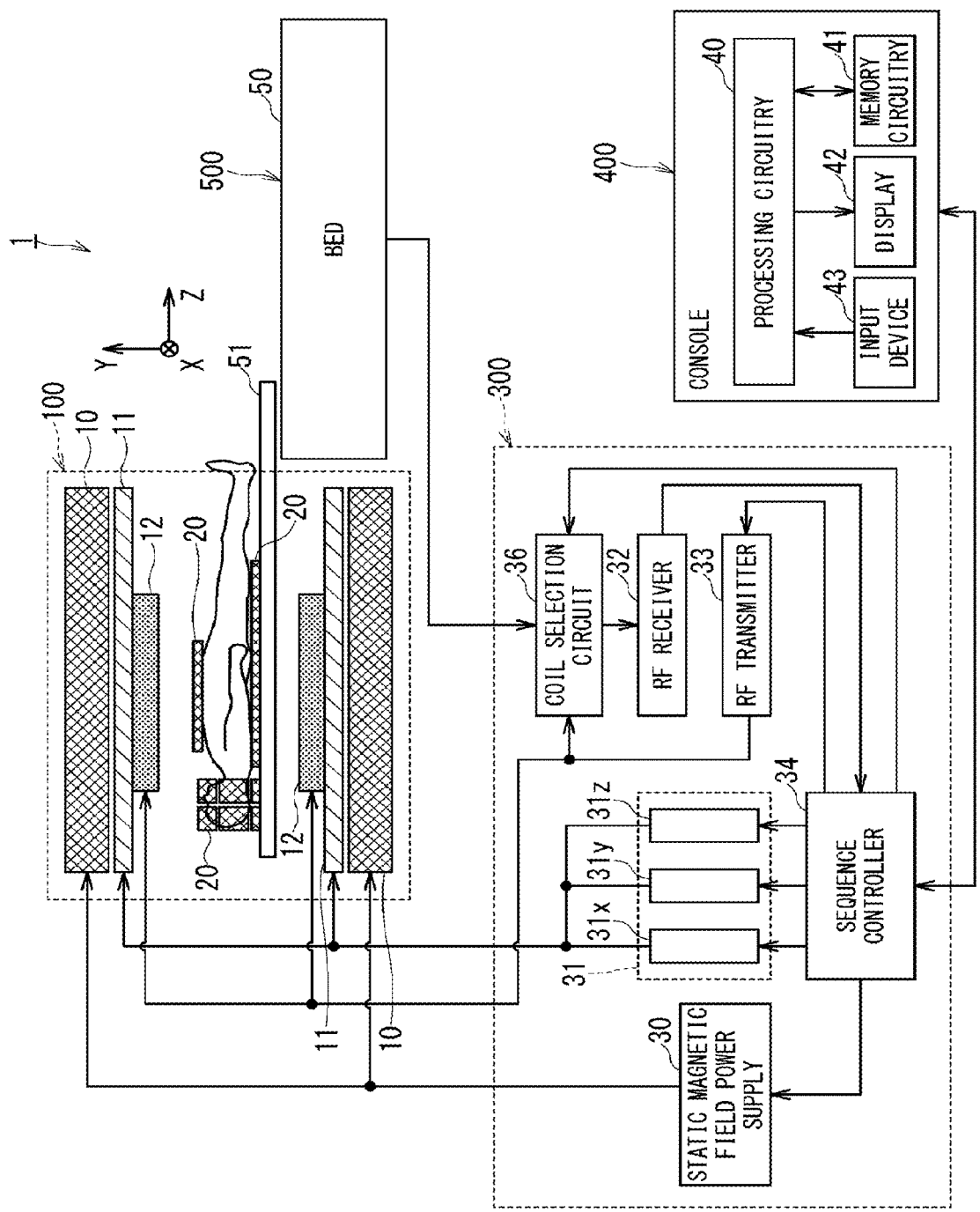
FIG. 1 is a block diagram illustrating overall configuration of an MRI apparatus according to the first embodiment.

FIG. 1 is a block diagram illustrating overall configuration of an MRI apparatus 1 of the first embodiment. The MRI apparatus 1 includes a gantry 100, a control cabinet 300, a console 400, a bed 500, and RF (Radio Frequency) coil 20.

The gantry 100 includes, a static magnetic field magnet 10, a gradient coil 11, and a WB (Whole Body) coil 12, and these components are included in a cylindrical housing. The bed 200 includes a bed body 50 and a table 51.

The control cabinet 300 includes a static magnetic field power supply 30, three gradient coil power supplies 31 (to be exact, 31x for an X-axis, 31y for a Y-axis, and 31z for a Z-axis), a coil selection circuit 36, an RF receiver 32, an RF transmitter 33, and a sequence controller 34.

The console 400 includes processing circuitry 40, memory circuitry 41, an input device 43, and a display 42. The console 400 functions as a host computer.

The static magnetic field magnet 10 of the gantry 100 is substantially in the form of a cylinder, and generates a static magnetic field inside a bore, into which an object, e.g., a patient is moved. The bore is a space inside the cylindrical structure of the gantry 100. The static magnetic field magnet 10 includes a superconducting coil inside, and the superconducting coil is cooled down to an extremely low temperature by liquid helium. The static magnetic field magnet 10 generates the static magnetic field by supplying the superconducting coil with the electric current provided from the static magnetic field power supply 30 in an excitation mode. Afterward, the static magnetic field magnet 10 shifts to a permanent current mode, and the static magnetic field supply 30 is separated. Once it enters the permanent current mode, the static magnetic field magnet 10 continues to generate a strong static magnetic field for a long time, e.g., over one year.

In FIG. 1, the blackly filled circle on the chest of an object indicates the position of the magnetic field center.

The gradient coil 11 is also substantially in the form of a cylinder, and is fixed to the inside of the static magnetic field magnet 10. This gradient coil 11 applies gradient magnetic fields to an object in the respective directions of the X-axis, the Y-axis, and the Z-axis, by using the electric currents supplied from the gradient coil power supplies 31x, 31y, and 31z.

The bed body 50 of the bed 500 can move the table 51 upward and downward in the vertical directions and can move the table 21 in the horizontal direction. The bed body 50 moves the table 51 with an object loaded thereon to a predetermined height before imaging. Afterward, when imaging, the bed body 50 moves the table 51 in the horizontal direction so as to move the object inside the bore.

The WB coil 12 is also referred to as a whole body coil, is shaped approximately in the form of a cylinder so as to surround an object, and is fixed to the inside of the gradient coil 11. The WB coil 12 applies each RF pulse transmitted from the RF transmitter 33 to an object, and receives MR (Magnetic Resonance) signals emitted from the object due to excitation of hydrogen nuclei.

As shown in FIG. 1, the MRI apparatus 1 includes RF coils 20 aside from the WB coil 12. Each of the RF coils 20 is a coil to be placed adjacent to a body surface of an object. Each of the RF coils 20 includes plural coil elements described below. Since these plural coil elements are arranged in an array inside each of the RF coils 20, these plural coil elements are sometimes collectively referred to as PAC (Phased Array Coils). Various types of RF coil are known as the RF coils 20.

For example, a body coil to be mounted on the chest, abdomen, and/or legs of an object as shown in FIG. 1 is known as a type of the RF coils 20. Additionally, a spine coil to be mounted on the back of an object as shown in FIG. 1 is known as a type of the RF coils 20. Further, a head coil used for imaging a head of an object, a foot coil used for imaging a foot of an object are also known as other types of the RF coils 20.

FIG. 1 illustrates a body coil, a spine coil, and a head coil of the above-described RF coils. Although many types of the RF coils 20 are receive-only surface coils, some types of head coil are configured to implement both functions of applying RF pulses and receiving MR signals. Each of the RF coils 20 are configured to be detachable from the table 51 via a cable.

The RF transmitter 33 generates RF pulses based on commands inputted from the sequence controller 34. The generated RE pulses are transferred to the WB coil 12 and applied to an object. MR signals are emitted from the object due to application of each RF pulse. These MR signals are received by the RF coils 20 or the WB coil 12.

The MR signals received by the RF coils 20, i.e., the MR signals detected by the respective coil elements inside each of the RF coils 20 are transferred to the coil selection circuit 36 via cables provided in the table 51 and the bed body 50.

The output pathway of each of the coil elements and/or the output pathway of the WB coil 12 is referred to as a channel. Thus, each of MR signals which are outputted from respective coil elements and/or the WB coil 12 is also referred to as a channel signal. The channel signal outputted from the WB coil 12 is also transferred to the coil selection circuit 36.

The coil selection circuit 36 selects channel signals outputted from the RF coils 20 or the channel signal outputted from the WB coil 12, according to a control signal inputted from the sequence controller 34 or the console 400.

The selected channel signals are transferred to the RF receiver 32. The RF receiver 32 performs A/D (Analog to Digital) conversion on the channel signals, i.e., MR signals, and outputs the digitized MR signals to the sequence controller 34. The digitized MR signals are also referred to as raw data. Incidentally, the A/D conversion of the MR signals may be performed inside each of the RF coils 20 or in the coil selection circuit 36.

The sequence controller 34 performs a scan of an object by driving the gradient coil power supplies 31x, 31y, and 31z, the RF transmitter 33, and the RF receiver 32, under the control of the console 400. The sequence controller 34 receives raw data from the RF receiver 32 by performing a scan, and then, the sequence controller 34 transfers the raw data to the console 400.

The sequence controller 34 includes non-illustrated processing circuitry. The processing circuitry of the sequence controller 34 is configured of hardware such as an FPGA (Field Programmable Gate Array), an ASIC (Application Specific Integrated Circuit), and a processor executing predetermined programs.

The console 400 includes memory circuitry 41, an input device 43, a display 42, and processing circuitry 40. The memory circuitry 41 is a memory medium including external memory devices such as a ROM (Read Only Memory), a RAM (Random Access Memory) a HDD (Hard Disk Drive), and an optical disc. The memory circuitry 41 stores various types of programs executed by a processor of the processing circuitry 40 in addition to various types of information and data.

The input device 43 is configured of, for example, a mouse, a keyboard, a trackball, and a touch panel, and includes various types of devices in order for an operator to input various types of information and data. The display 42 is a display device such as a liquid crystal display panel, a plasma display panel, and an organic EL (light emitting) display.

The processing circuitry 40 is, for example, a circuit equipped with a CPU and/or a special-purpose or general-purpose processor. This processor implements various types of functions described below by executing various types of programs stored in the memory circuitry 41. The processing circuitry 40 may be configured as hardware such as an FPGA and an ASIC. Various types of functions of the processing circuitry 40 can be implemented by such hardware as well. Additionally, the processing circuitry 40 may implement various types of functions by combining hardware processing and software processing by a processor and programs.

Figure 2B:
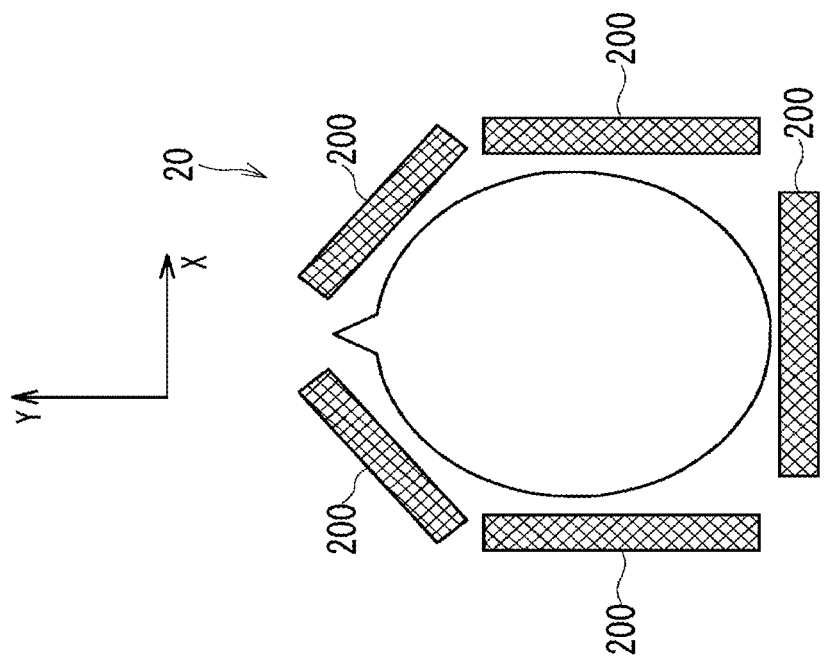
FIG. 2A and FIG. 2B are schematic diagrams illustrating configuration of an RF coil for imaging a head.
Figure 2A:
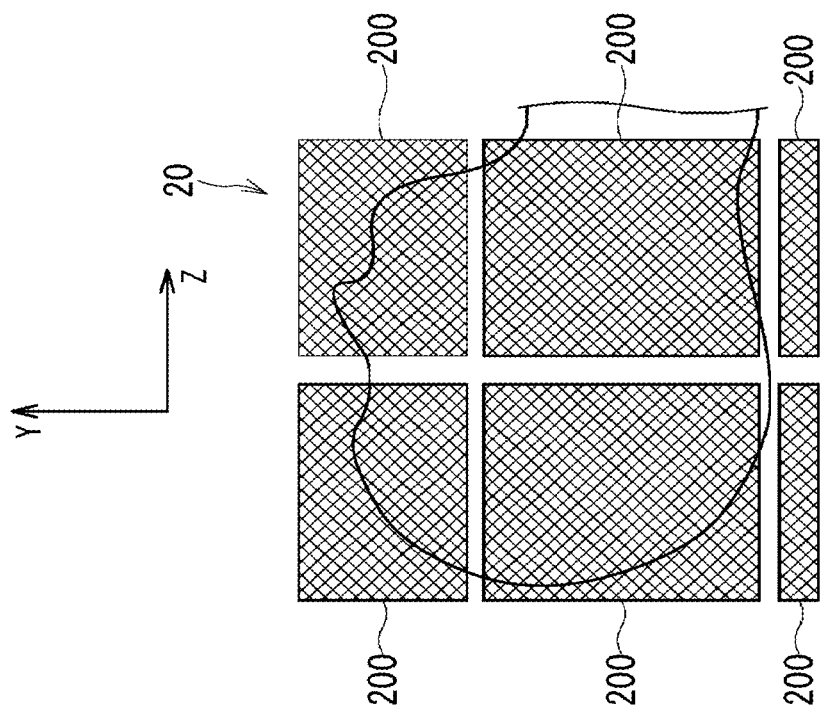

FIG. 2A and FIG. 2B are schematic diagrams illustrating configuration of the RF coil 20 for imaging a head. The RF coil 20 as a head coil is attached to the object so as to cover an area of the head as shown in FIG. 1, FIG. 2A, and FIG. 2B. Each of the RF coils 20 such as a body coil, a head coil, and a spine coil is equipped with plural coil elements 200 inside. In the head coil illustrated in FIG. 2A and FIG. 2B, five coil elements 200 are arranged around an axial plane of the head as shown in FIG. 2B. Two rows of these five coil elements 200 (i.e., a total of ten coil elements) are arranged along the head-foot direction, i.e., along the Z-axis direction. Note that the head coil shown in FIG. 2A and FIG. 2B is only one of possible embodiments and the number of the coil elements 200 and its arrangement are not limited to the aspect shown in FIG. 2A and FIG. 2B.

Figure 3:
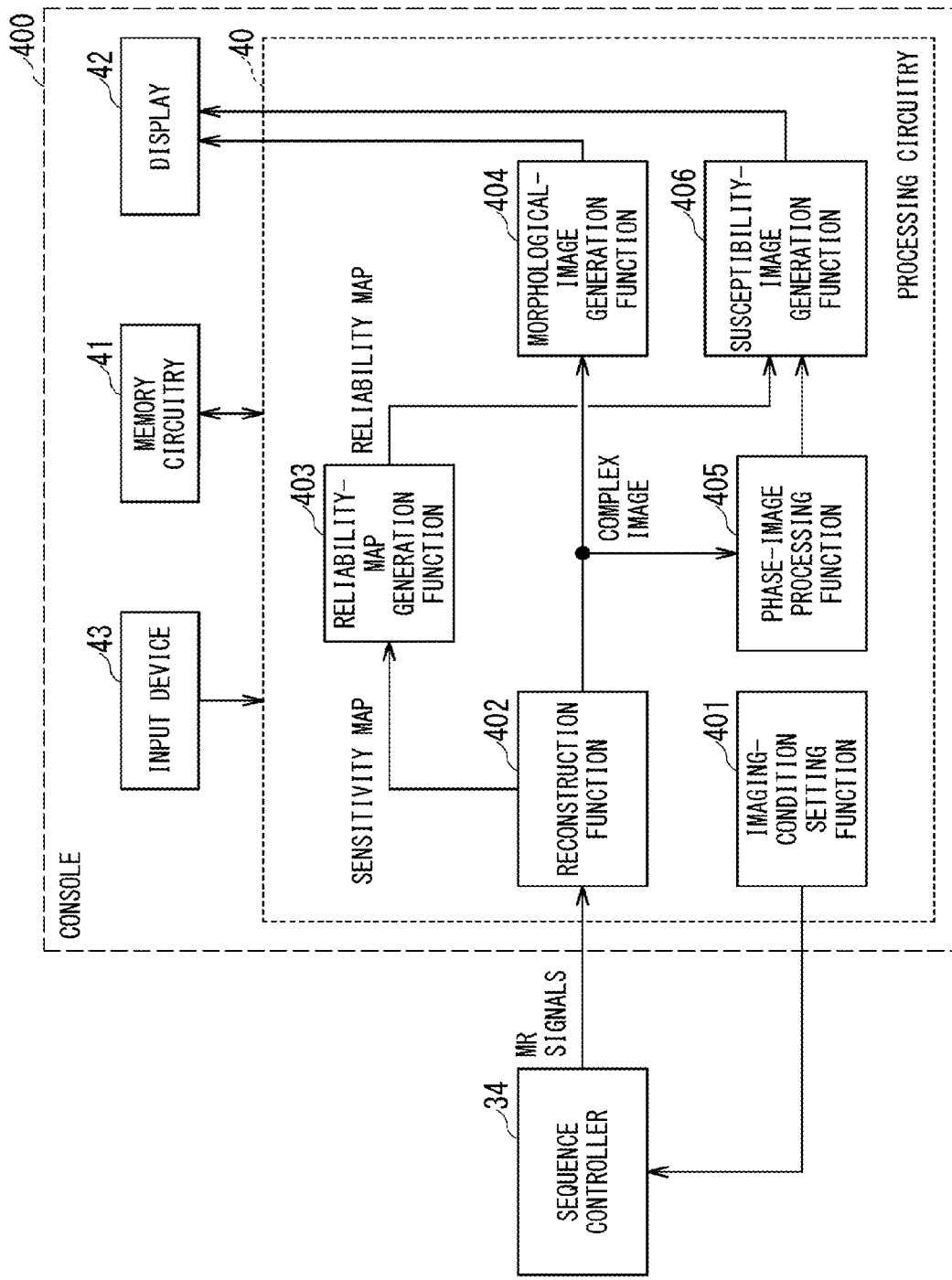
FIG. 3 is a functional block diagram of the MRI apparatus of the first embodiment.

FIG. 3 is a block diagram illustrating functions implemented mainly by the console 400 of the MRI apparatus 1 in the first embodiment. Additionally, FIG. 4 is a flowchart illustrating processing performed by the MRI apparatus 1 in the first embodiment.

As shown in FIG. 3, the processing circuitry 40 of the console 400 implements an imaging-condition setting function 401, a reconstruction function 402, a reliability-map generation function 403, a morphological-image generation function 404, a phase-image processing function 405, and a susceptibility-image generation function 406. The processing circuitry 40 includes, for example, a processor which implements each of the above-described functions by executing predetermined programs stored in the memory circuitry 41. Each of the above-described functions will be described in accordance with the flowchart shown in FIG. 4.

Figure 4:
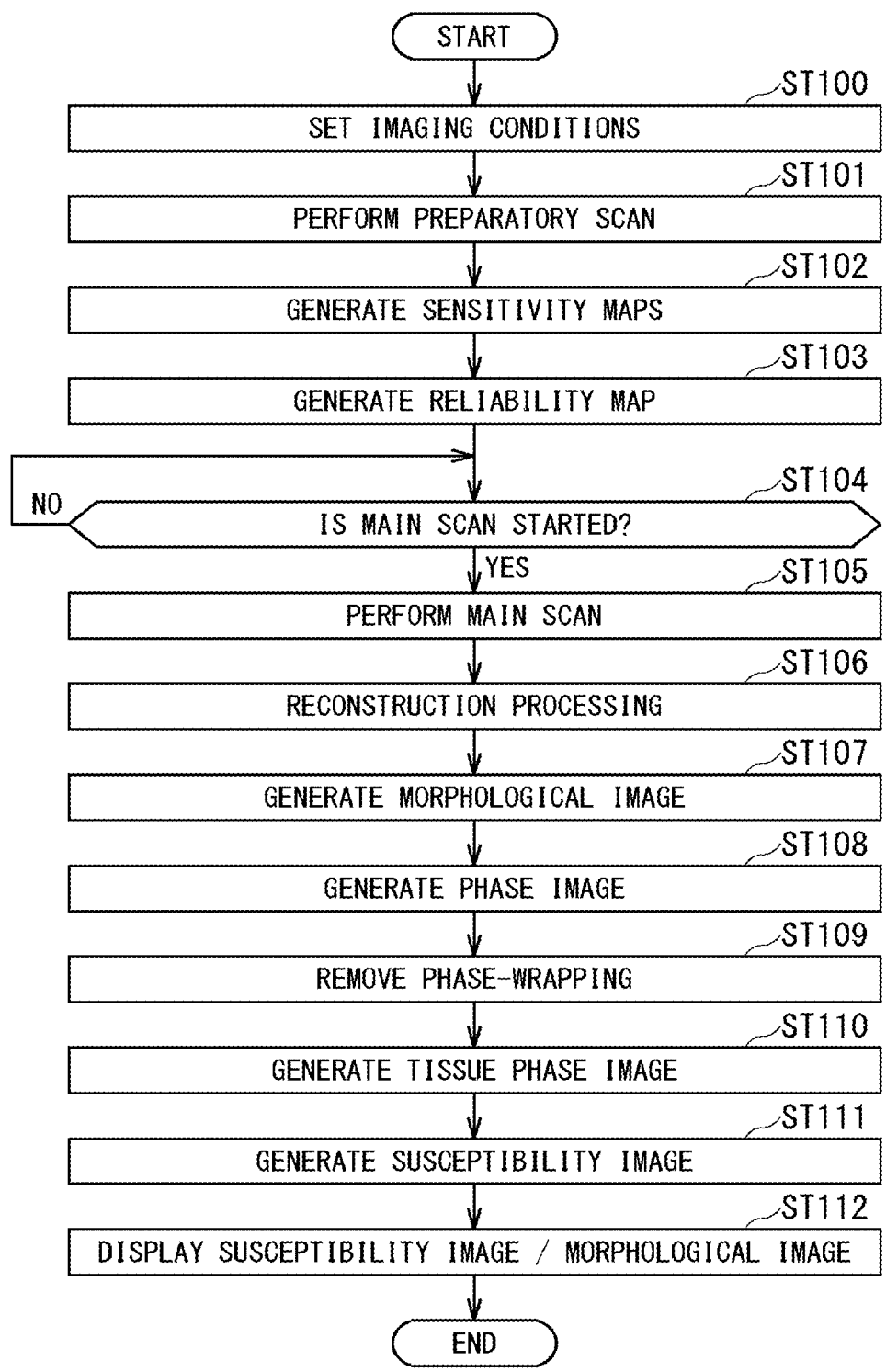
FIG. 4 is a flowchart illustrating processing performed by the MRI apparatus of the first embodiment.

The flowchart shown in FIG. 4 illustrates a case in which a fast imaging technique using parallel imaging is applied as a main scan for obtaining diagnostic images of an object. The MRI apparatus 1 of the first embodiment, however, can be applied to other imaging techniques aside from parallel imaging.

In parallel imaging, plural reduced images (i.e., plural aliased images), corresponding to respective coil elements 200 in each of the RF coils 20, are generated. Since these reduced images are generated from data reduced (i.e., under-sampled) in the phase encode direction, aliasing is included in each of these reduced images. Each of the reduced images in which aliasing is included is subjected to unfolding processing by using information of the sensitivity maps of the respective coil elements 200, and then an image without aliasing is generated. As described above, sensitivity maps indicating sensitivity distribution of the respective coil elements 200 with respect to an object are necessary in parallel imaging. For this reason, a preparatory scan is performed before the main scan, and sensitivity maps are generated by using MR signals acquired from an object in this preparatory scan.

In FIG. 4, the processing of the step ST100 corresponds to the imaging-condition setting function 401. In the step ST100, the processing circuitry 40 receives setting information on imaging conditions inputted by an operator. The memory circuitry 41 stores default values of various imaging parameters of pulse sequence sets for a preparatory scan and a main scan, depending on each imaging purpose and for each anatomical imaging part. For example, default values of imaging parameters such as TR (Repetition Time), TE (Echo Time), a flip angle, slice thickness, and slice number are stored for each pulse sequence set.

The processing circuitry 40 shows pulse sequence set for each imaging purpose and for each anatomical imaging part to an operator via a GUI (Graphical User Interface), and thereafter receives input of selecting and/or changing a pulse sequence set and imaging parameters from the operator. In this manner, the processing circuitry 40 determines respective pulse sequence sets performed in a preparatory scan and a main scan, and their imaging parameters as imaging conditions. The processing circuitry 40 sets the determined imaging conditions on the sequence controller 34.

When a command to start the preparatory scan is inputted by an operator after setting imaging conditions, the sequence controller 34 causes respective components of the MRI apparatus 1 to perform the preparatory scan according to the determined imaging conditions of the preparatory scan in the step ST101.

The processing circuitry 40 acquires MR signals received by respective coil elements 200 and MR signals received by the WB coil 12 in the preparatory scan via the sequence controller 34. A scan for shimming and a scan for acquiring scout images may be included in the preparatory scan.

The processing of the step ST102 corresponds to the reconstruction function 402. In the step ST102, the processing circuitry 40 reconstructs MR signals received by respective coil elements 200 and MR signals received by the WB coil 12, so as to generate sensitivity maps each of which indicates sensitivity distribution of each of the coil elements 200. For example, the processing circuitry 40 generates sensitivity maps of the respective coil elements 200 by dividing intensity distribution of the reconstructed image of each of the coil elements 200 by intensity distribution of the reconstructed image of the WB coil 12. Each of the generated sensitivity maps is stored in the memory circuitry 41. The sensitivity maps are used for unfolding processing in parallel imaging, and are also used for generating a reliability map in the next the step ST103 in the first embodiment.

Incidentally, each reliability map in the description of the first embodiment and other embodiments is an aspect of a weighting map recited in the claims.

The processing of the step ST103 corresponds to the reliability-map generation function 403. In the step ST103, the processing circuitry 40 generates one reliability map from plural sensitivity maps generated in the step ST102. More specifically, the processing circuitry 40 generates spatial distribution of one geometry factor, i.e., one geometry factor map, from the plural sensitivity maps. Further, the processing circuitry 40 defines the inverse of the geometry factor map, i.e., the inverse map of the geometry factor as a reliability map.

Figure 5:
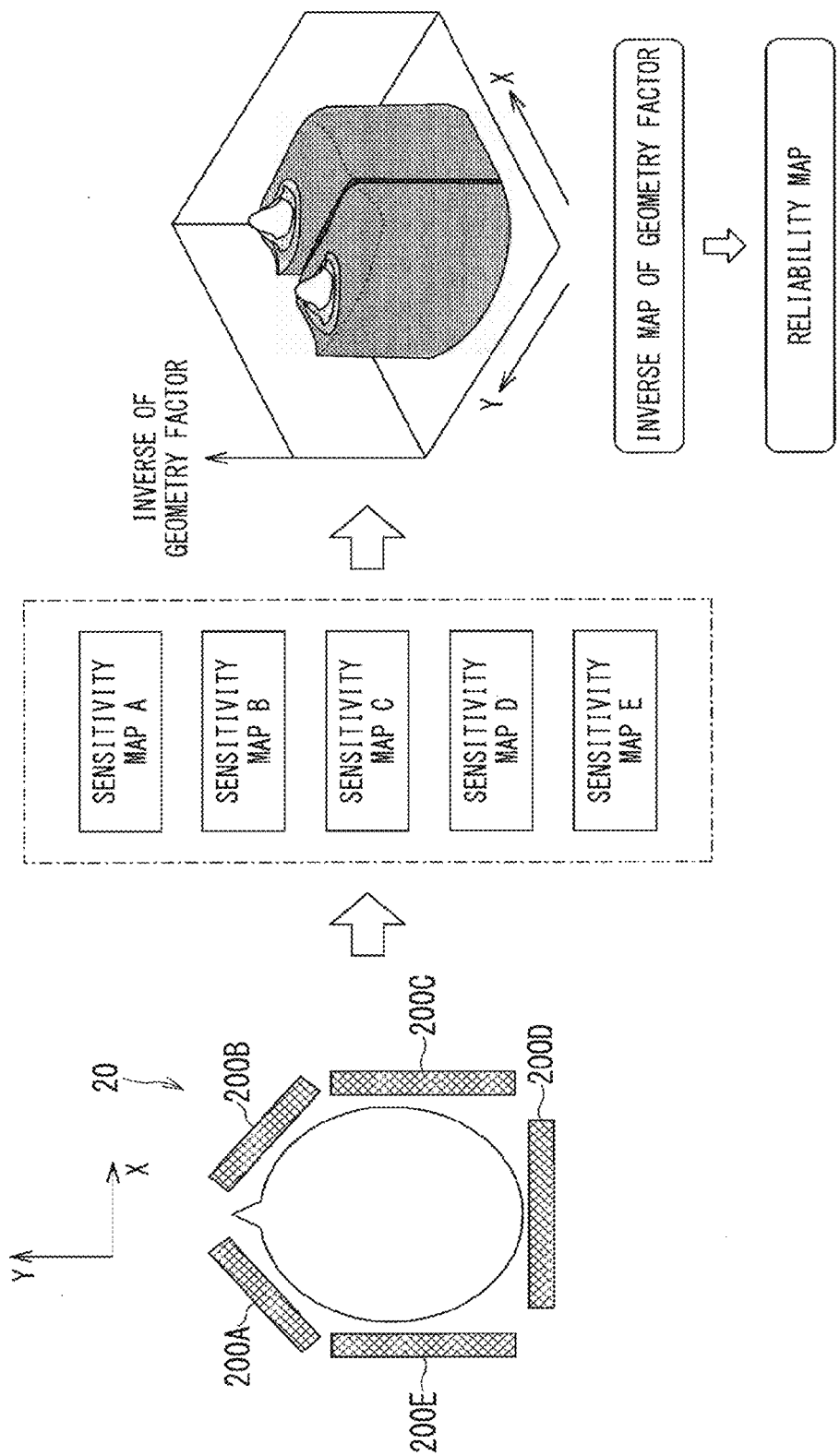
FIG. 5 is a schematic diagram illustrating a concept of processing of generating five sensitivity maps and generating one reliability map from these five sensitivity maps.

FIG. 5 is a schematic diagram illustrating a concept of processing of generating five sensitivity maps A, B, C, D, and E respectively corresponding to five coil elements 200A to 200E of the head coil, and generating one reliability map from these five sensitivity maps A to E.

A method disclosed, for example, in the Document 2 (K. P. Pruessmann et al., "SENSE: Sensitivity Encoding for Fast MRI", Magnetic Resonance in Medicine 42:952-962 (1999)) may be used for generating spatial distribution of one geometry factor from plural sensitivity maps. Additionally, in the Document 2, it is disclosed that an SNR (Signal to Noise Ratio) of an unfolded image of parallel imaging based on a SENSE method is in proportion to the inverse of a geometry factor. Thus, the reliability map generated in the step ST103 can be considered to be a map having a higher value at a position where an SNR in the unfolded image generated in parallel imaging is higher. Additionally, the reliability map generated in the step ST103 also can be considered to be a map having higher value at a position where a signal value of the unfolded image in parallel imaging is calculated with higher accuracy.

Although the reliability map shown in FIG. 5 corresponds to a slice of one axial plane (X-Y plane), a three-dimensional reliability map can be generated by combining plural reliability maps corresponding to respective slices in the Z-axis direction.

Next, when a command to start the main scan is inputted by an operator (i.e., YES in the step ST104), the sequence controller 34 causes the respective components of the MRI apparatus 1 to perform the main scan under its determined imaging conditions in the step ST105. Here, fast imaging based on parallel imaging is performed as the main scan.

The processing of the step ST106 corresponds to the reconstruction function 402. In the step ST106, the processing circuitry 40 reconstructs the acquired MR signals detected by respective coil elements 200 so as to generate reduced images which correspond to the respective coil elements 200 and include aliasing. Afterward, the processing circuitry 40 generates an unfolded image in which aliasing is removed, by unfolding the respective reduced images using the sensitivity maps. The unfolded image at this stage is a complex image in which each pixel value is a complex number.

The processing of the step ST107 corresponds to the morphological-image generation function 404. In the step ST107, the processing circuitry 40 generates a morphological image, which is used for usual image-diagnosis, by converting a complex number of each pixel of the unfolded image into intensity (e.g., an absolute value or a square value).

The processing of the steps ST108 to ST110 corresponds to the phase-image processing function 405.

In the step ST108, the processing circuitry 40 generates a phase image by converting a complex number of each pixel of the unfolded image into phase amount θ. For example, the processing circuitry 40 generates a phase image by performing conversion of $\theta = \tan^{-1}$ (imaginary part/real part).

Figure 6:
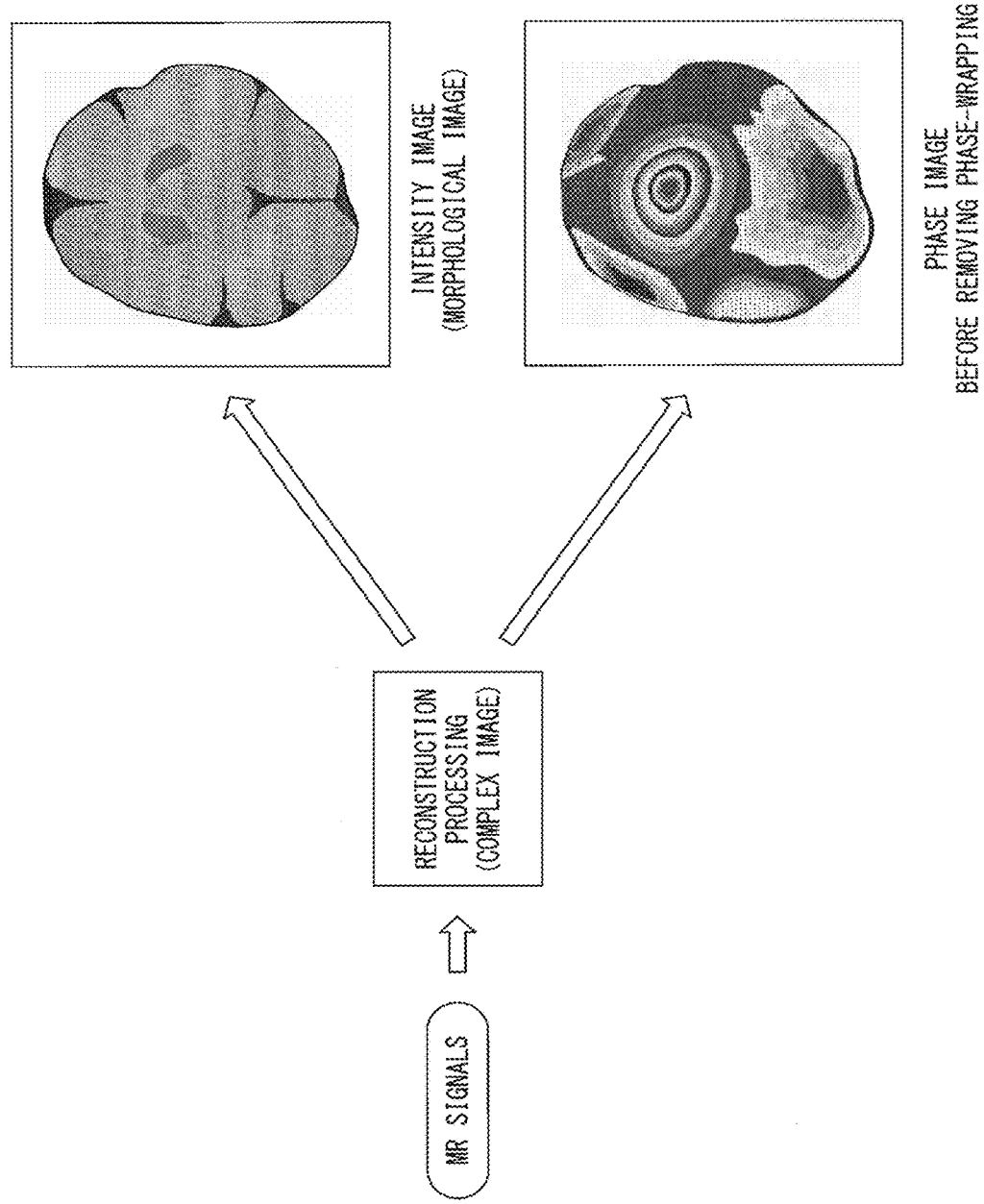
FIG. 6 is a schematic diagram illustrating a concept of the processing of the steps ST106 to ST108 in FIG. 4 in which a morphological image and a phase image in the brain are generated from MR signals acquired in the main scan.

FIG. 6 is a schematic diagram illustrating a concept of the processing of the steps ST106 to ST108 in which a morphological image and a phase image in the brain are generated from MR signals acquired in the main scan. As shown in the lower right part of FIG. 6, the phase image generated in the step ST108 has phase wrappings wrapped within the range of ±π.

Figure 7:
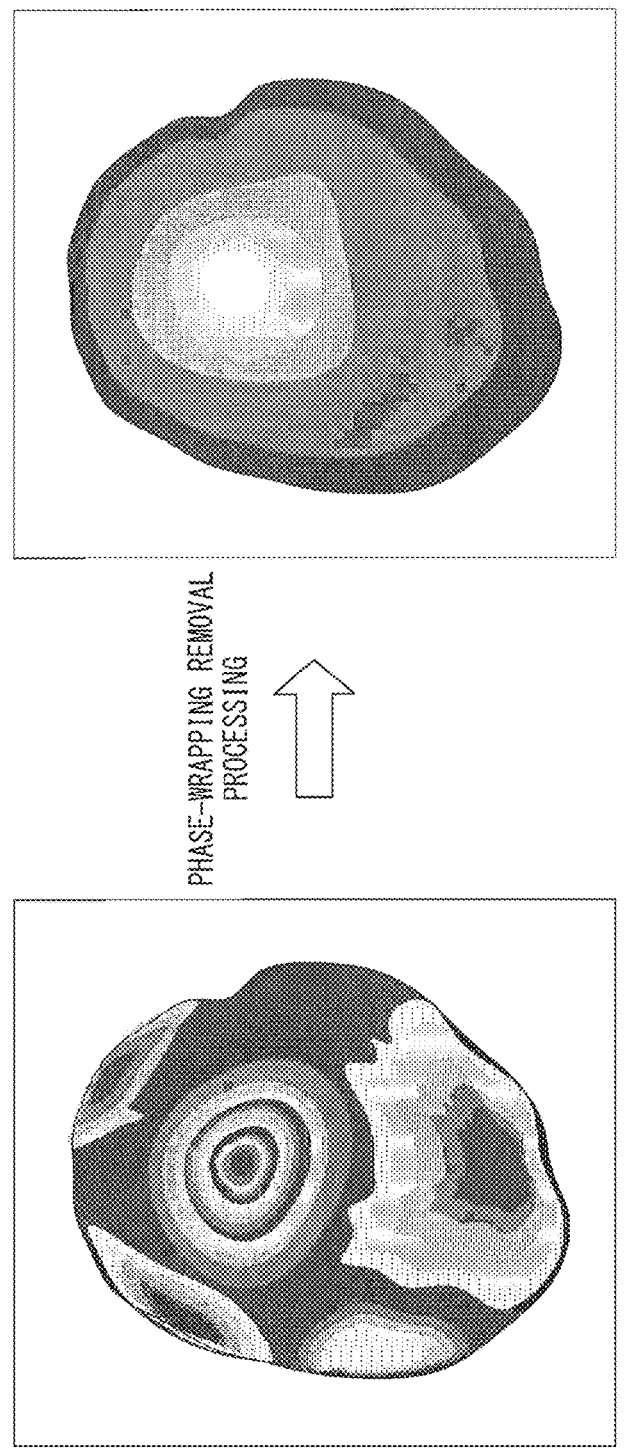
FIG. 7 is a schematic diagram illustrating a cerebral phase image before phase-wrapping removal and a cerebral phase image after phase-wrapping removal.

In the step ST109, the processing circuitry 40 performs phase-wrapping removal processing on the phase image obtained in the step ST108. FIG. 7 is a schematic diagram illustrating a cerebral phase image before phase-wrapping removal (i.e., the same image as the lower right part of FIG. 6) on the left side and a cerebral phase image after phase-wrapping removal on the right side.

As phase-wrapping removal processing, a conventional technique known in the field of, e.g., MRI and SAR (Synthetic Aperture Radar) may be used. For example, the processing circuitry 40 can perform phase-wrapping removal processing by using a known technique such as a region growing method, a Laplacian method, or a graph cut segmentation method.

Next, in the step ST110, the processing circuitry 40 performs background field removal processing on the phase image in which phase-wrapping is removed. In the phase image after phase-wrapping removal, a phase induced by magnetic susceptibility of each body tissue and a phase induced by a background magnetic field are superimposed with each other. A phase induced by a background magnetic field is much larger than a phase induced by magnetic susceptibility of each body tissue, e.g., the former is ten times larger than the latter. Thus, in order to accurately calculate magnetic susceptibility of each body tissue, background field removal processing, i.e., processing of removing a background-field-induced phase from a phase image subjected to phase-wrapping removal is necessary.

As background field removal processing, various techniques such as a method of applying a high-pass filter, a SHARP (Sophisticated Harmonic Artifact Reduction on Phase data) method including an advanced SHARP method and a RESHARP (Regularization-Enabled SHARP) method, and a PDF (Projection onto Dipole Field) method disclosed in the following Documents 3, 4, and 5 may be used.

[Document 3] Y. Wang et al., "Quantitative Susceptibility Mapping (QSM): Decoding MRI Data for a Tissue Magnetic Biomarker", Magnetic Resonance in Medicine 73: 82-101 (2015)

[Document 4] T. Liu et al., "A novel background field removal method for MRI using projection onto dipole fields (PDF)", NMR Biomed. 2011 November; 24 (9): 1129-1136

[Document 5] F. Schweser et al., "A Novel Approach for Separation of Background Phase in SWI Phase Data Utilizing the Harmonic Function Mean Value Property", ISMRM 2010 p. 142

The processing circuitry 40 performs one of the above-described types of background field removal processing on the phase image subjected to phase-wrapping removal so as to generate a phase image in which influence of a background magnetic field is removed, i.e., a tissue phase image. FIG. 8 is a schematic diagram illustrating a cerebral phase image after phase-wrapping removal (i.e., the same image one the right side of FIG. 7) on the left side and a cerebral tissue phase image after background field removal processing on the right side.

The processing of the next step ST111 corresponds to the susceptibility-image generation function 406. In the step ST111, the processing circuitry 40 generates a quantitative susceptibility image which quantitatively indicates magnetic susceptibility inside the body of the object, from the tissue phase image with the use of the reliability map. Specifically, the processing circuitry 40 generates a quantitative susceptibility image by calculating magnetic susceptibility $\chi$ of each pixel from the phase θ of each pixel of the tissue phase image under the method as follows.

According to the Document 1 (T. Liu et al., "Morphology Enabled Dipole Inversion (MEDI) from a Single-Angle Acquisition: Comparison with COSMOS in Human Brain Imaging", MRM 66: 777-783 (2011)), the relationship indicated by the following the formulas (1) and (2) holds between the phase θ and the magnetic susceptibility $\chi$ in the tissue phase image.

$$\delta = d * \chi \qquad \text{Formula (1)}$$

$$\delta = -\frac{\theta}{\gamma \cdot B_0 \cdot TE} \qquad \text{Formula (2)}$$

In the formula (1), $\chi$ is magnetic susceptibility and d is a coefficient which is referred to as dipole kernel and indicates behavior of a magnetic dipole. The symbol * indicates convolutional integration. δ is referred to as a local field map, and a value obtained by dividing the phase θ of the tissue phase image by the gyromagnetic ratio γ, magnetic field intensity $B_0$, and the echo time TE as shown in the formula (2).

The convolutional integration in the formula (1) can be converted into multiplication by applying Fourier transform as shown by the following formula (3).

$$\delta = F^{-1}[DF[\chi]] \qquad \text{Formula (3)}$$

Here, F[ ] indicates Fourier transform, and $F^{-1}$[ ] indicates inverse Fourier transform. Additionally "D" in the formula (3) is Fourier transform of d in the formula (1) and is indicated by the following formula (4) using the position coordinate of k-space (kx, ky, kz).

$$D = \frac{1}{3} - \frac{k_z^2}{k_x^2 + k_y^2 + k_z^2} \qquad \text{Formula (4)}$$

As is clear from the formula (3), Fourier transform of δ is equal to the product of D and F[χ], i.e., F[δ]=DF[χ]. Thus, when F[χ] is determined by dividing Fourier transform of δ by D and then inverse Fourier transform is applied to the determined F[χ], magnetic susceptibility χ can be calculated. However, as is clear from the formula (4), the inverse of D becomes zero when the condition shown by the following formula (5) is satisfied.

$$\frac{1}{3} = \frac{k_z^2}{k_x^2 + k_y^2 + k_z^2} \qquad \text{Formula (5)}$$

Thus, the method of determining F[χ] by applying division with D is becomes an ill-posed problem.

As acceptable solution to the above-described ill-posed problem, there is a method of stably obtaining approximate solution of magnetic susceptibility χ by applying optimization processing in which a regularization term such as spatial smoothness of magnetic susceptibility χ and/or edge structure is added based on the following formula (6).

$$f(\chi) = \|W \cdot (\delta - F^{-1}[DF[\chi]])\|_2 + \lambda \cdot \|\chi\|_p \qquad \text{Formula (6)}$$

Here, the first term on the right-hand side of the formula (5) a data term indicating matching degree of the formula (3), the second term on the right-hand side of the formula (6) is a regularization term indicating spatial smoothness of magnetic susceptibility χ. Additionally, λ indicates a regularization parameter, and W indicates a weighting coefficient, and p indicates a norm.

The magnetic susceptibility χ can be determined by optimizing the right-hand side of the formula (6). Although a case of minimizing the right-hand side will be described in the present embodiment, an optimization method of determining the magnetic susceptibility χ is not limited to this method. For example, various optimization methods such as a Newton's method, a steepest descent method, a conjugate gradient method, a nonlinear conjugate gradient method, a penalty method, and an ADMM (Alternating Direction Method of Multipliers) may be used.

The weighting coefficient W in the formula (6) is a coefficient having spatial distribution, and order of spatial distribution may be two-dimensional or three-dimensional. For example, a two-dimensional weighting coefficient W(x, y) may be used when a quantitative susceptibility image to be generated is two-dimensional, and a three-dimensional weighting coefficient W(x, y, z) may be used when a quantitative susceptibility image to be generated is three-dimensional.

In the case of the MRI apparatus 1 of the first embodiment, the reliability map generated from the sensitivity maps of the respective coil elements 200 in the step ST103 is used as the weighting coefficient W in the formula (6). Hereinafter, a reliability map is sometimes referred to as a reliability map W (x, y, z). According to the MRI apparatus 1 of the first embodiment described so far, the reliability map W(x, y, z) is assumed to be calculated from inverse of the geometry factor map.

As described above, an SNR of an unfolded image obtained by parallel imaging of a SENSE method is in proportion to inverse of a geometry factor. Thus, an SNR of a tissue phase image derived from an unfolded image is also in proportion to inverse of a geometry factor. In the first embodiment, the inverse of the geometry factor map is indicated as the weighting coefficient W in the formula (6) for calculating magnetic susceptibility χ from such a tissue phase image. As a result, influence of a phase image with a high SNR is enhanced whereas influence of a phase image with a low SNR is reduced in calculation of a quantitative susceptibility image, and a quantitative susceptibility image can be generated with high accuracy. In other words, even if there exist differences in SNR between pixels of a tissue phase image, magnetic susceptibility of every pixel of a quantitative susceptibility image can be appropriately calculated.

Figure 9:
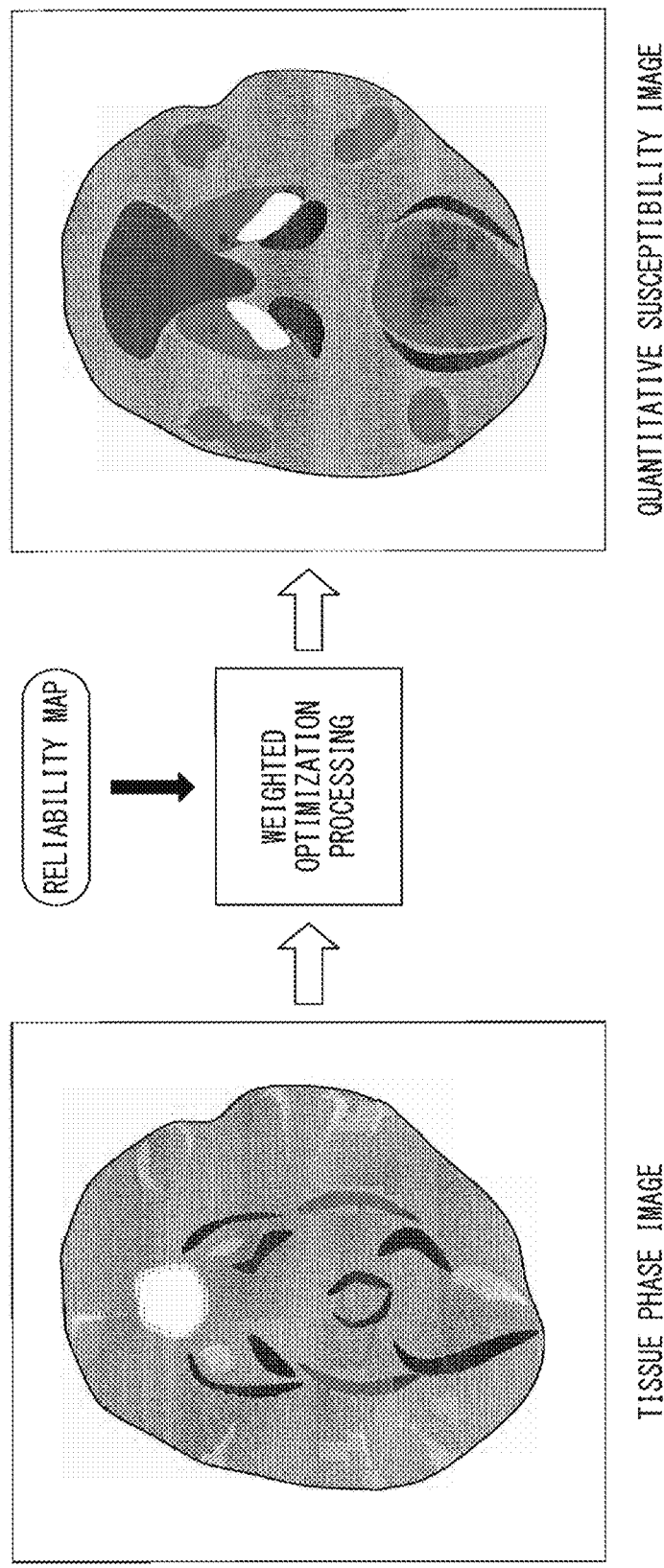
FIG. 9 is a schematic diagram illustrating a cerebral tissue phase image and a cerebral quantitative susceptibility image.

FIG. 9 is a schematic diagram illustrating a cerebral tissue phase image (i.e., the right side image in FIG. 8) on the left side and a cerebral quantitative susceptibility image generated in the above-described manner on the right side.

Figures 10A, 10B:
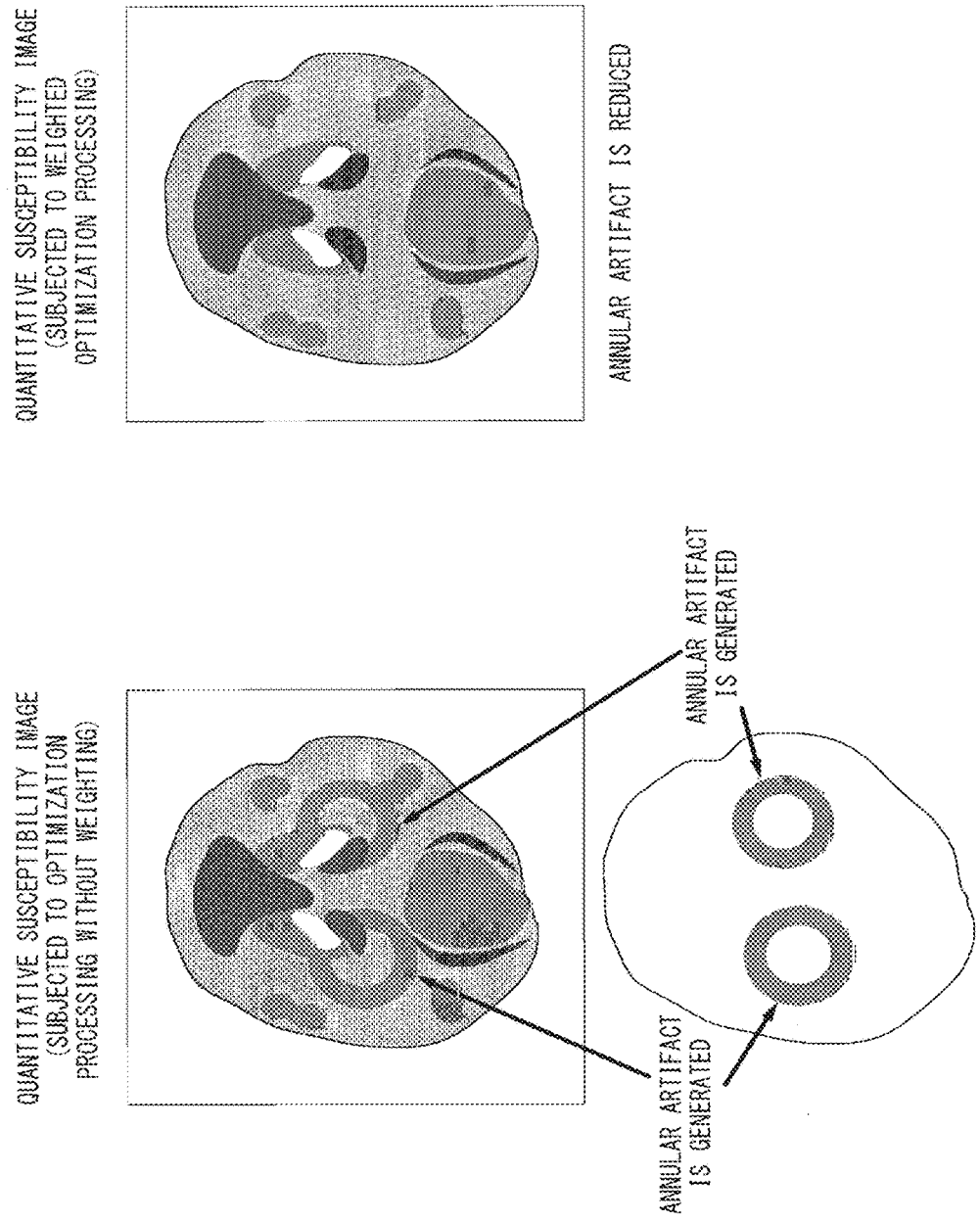
FIG. 10A is a schematic diagram illustrating a quantitative susceptibility image generated by optimization processing without weighting.
FIG. 10B is a schematic diagram illustrating a quantitative susceptibility image generated by weighted optimization processing based on a reliability map.

FIG. 10A is a schematic diagram illustrating a quantitative susceptibility image generated by optimization processing without weighting (i.e., by assuming that the weighting coefficient W of the formula (6) is 1).

FIG. 10B is a schematic diagram illustrating a quantitative susceptibility image generated by the above-described weighted optimization processing based on the reliability map.

As shown in FIG. 10A, two annular artifacts are generated in the central part of a cerebral quantitative susceptibility image generated without weighting. By contrast, as shown in FIG. 10B, such an artifact is not generated in the cerebral quantitative susceptibility image generated by weighting. It is considered that a pixel with a low SNR is included in a phase image and an artifact is generated in an annular region whose center is the pixel with a low SNR by being influenced by the pixel with a low SNR in the process of generating a quantitative susceptibility image from such a phase image.

Additionally, when pixels with a low SNR are dispersed in a phase image, it is also considered that the quantitative susceptibility image generated from this phase image is blurred over its entire region. However, a quantitative susceptibility image of high image quality without any blur or artifact can be generated by performing weighted optimization processing based on a reliability map in the first embodiment.

In the Document 1, a method of determining a weighting coefficient from plural images obtained by plural main scan corresponding to respective echo times IF being different from each other is disclosed. By contrast, since the weighting coefficient, i.e., the reliability map is calculated independent of the main scan in the first embodiment, it is enough to perform the main scan only once. Thus, in the first embodiment, imaging time is shortened compared with the method disclosed in the Document 1.

Returning to FIG. 4, in the step ST112, the processing circuitry 40 causes the display 42 to display the generated quantitative susceptibility image.

Figure 11:
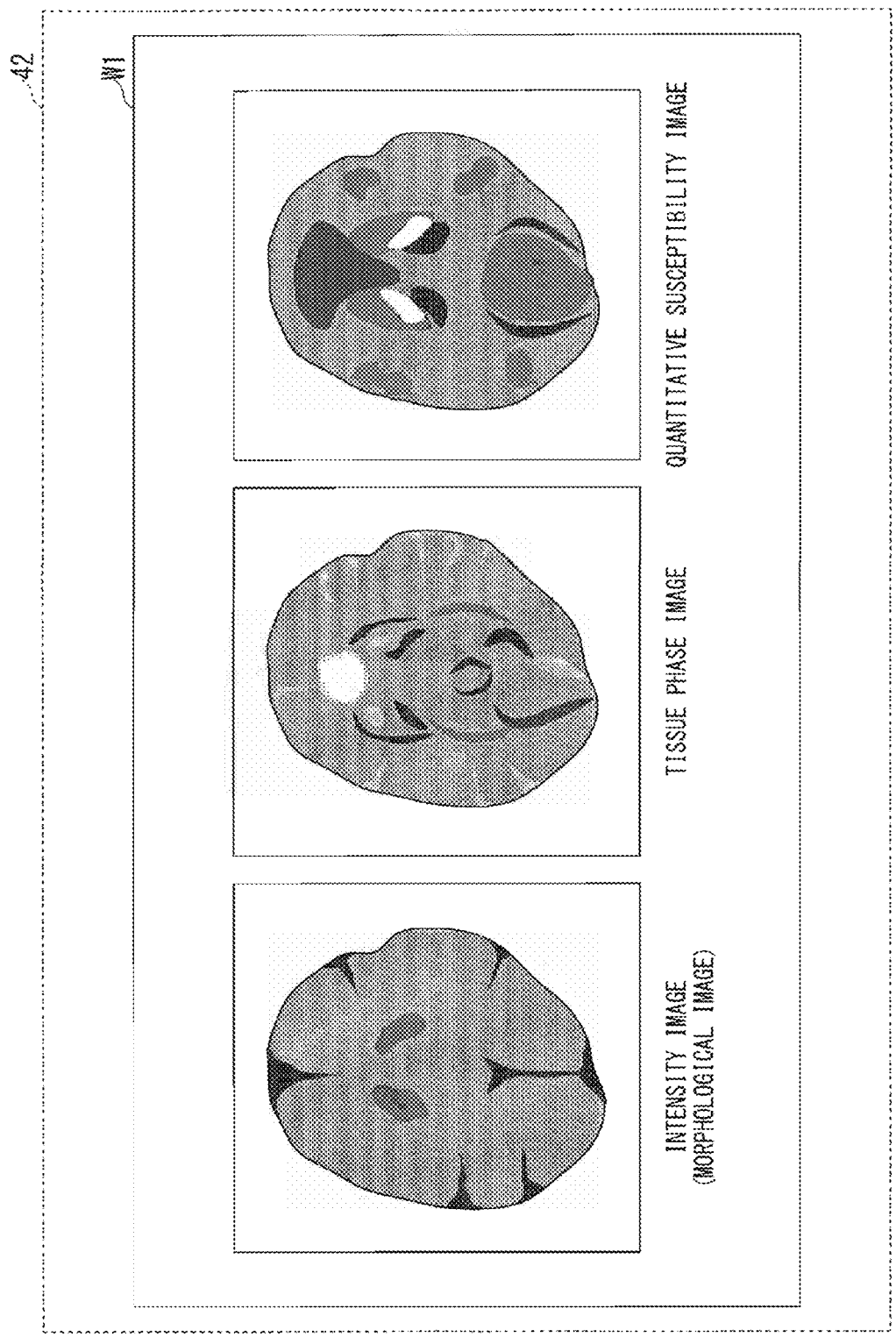
FIG. 11 is a schematic diagram illustrating display of a quantitative susceptibility image on an image display window of a display.

FIG. 11 is a schematic diagram illustrating display of a quantitative susceptibility image on an image display window W1 of the display 42. As shown in FIG. 11, the quantitative susceptibility image may be displayed so that the quantitative susceptibility image can be contrasted with the morphological image generated in the step ST107. For example, both images may be displayed side-by-side. As another embodiment, display of the quantitative susceptibility image and display of the morphological image may be temporally switched. In addition to these two images, the tissue phase image may be displayed. Further, intensity, phase, and magnetic susceptibility corresponding to each coordinate position of each image may be displayed by value or graphically displayed.

Moreover, each pixel value of the tissue phase image and/or the quantitative susceptibility image may be multiplied by each intensity signal value of the morphological image, or each intensity signal value of the morphological image may be subtracted from each pixel value of the tissue phase image and/or the quantitative susceptibility image.

Additionally or alternatively, a value obtained by multiplying each intensity signal value of each pixel of the morphological image by a predetermined coefficient may be subtracted from each pixel value of the tissue phase image and/or the quantitative susceptibility image. Similarly, each pixel value of the tissue phase image and/or the quantitative susceptibility image may be multiplied by a value obtained by multiplying each intensity signal value of each pixel of the morphological image by a predetermined coefficient.

Furthermore, the quantitative susceptibility image may be colorized and be superimposed on the morphological image which is a gray-scale image so that the superimposed image is displayed.

(First Modification of First Embodiment)

The weighting coefficient W based on the reliability map may be applied not to the data term but to the regularization term as shown in the following formula (7).

$$f(\chi) = \|(\delta - F^{-1}[DF[\chi]])\|_2 + \lambda \cdot \|W \cdot \chi\|_p \quad \text{Formula (7)}$$

Additionally or alternatively, the weighting coefficient W based on the reliability map may be applied to both of the data term and the regularization term as shown in the following formula (8).

$$f(\chi) = \|W \cdot (\delta - F^{-1}[DF[\chi]])\|_2 + \lambda \cdot \|W \cdot \chi\|_p \quad \text{Formula (8)}$$

(Second Modification of First Embodiment)

Although a reliability map is assumed to be a map of inverse of a geometry factor in the above description, a reliability map is not limited to this type. It is enough that a reliability map reflects an SNR or spatial distribution of signal intensity of the original image from which the quantitative susceptibility image is calculated.

For example, a sensitivity map used for calculating a geometry factor may be used as a reliability map. Additionally, one sensitivity map of the entirety of the RF coils 20 may be generated by composing sensitivity maps of respective coil elements 200 of the RF coils 20, and this composed sensitivity map may be used as a reliability map.

Moreover, in an imaging technique in which parallel imaging is not included, a preparatory scan for generating sensitivity maps is not performed in some cases. In those cases, a sensitivity map is not generated and thus a geometry factor cannot be calculated. In those cases, a distance map based on distance of each of the RF coils 20 or each of the coil elements 200 from the magnetic field center may be used as a reliability map. A distance map is, for example, a map whose value is maximized at the magnetic field center and becomes smaller at a position more separated from the magnetic field center.

When an object is imaged, in general, the object is placed inside the bore so that the center of an ROI (Region Of Interest) is positioned at the magnetic field center. Additionally, the RF coil 20 used for imaging is arranged to a position where the central position thereof is located substantially at the magnetic field center. Moreover, when predetermined number of coil elements 200 are selected from the RF coils 20, coil elements 200 close to the magnetic field center are selected. As a result, an SNR or signal intensity of an obtained image becomes higher at a position (i.e., pixel) closer to the magnetic field center and becomes lower at a position more separated from the magnetic field center. Accordingly, the distance map based on the distance from the magnetic field center reflects an SNR or spatial distribution of signal intensity of the original image from which a quantitative susceptibility image is calculated, and thus, the distance map is appropriate for a reliability map. Furthermore, the method of generating a reliability map based on a distance map is effective for imaging a region widely extending in the head-foot direction (i.e., the Z-axis direction) such as an abdomen, a chest, and legs.

Figure 12:
FIG. 12 is a schematic diagram illustrating some methods of generating a reliability map.

FIG. 12 is a schematic diagram illustrating some methods of generating a reliability map. As shown in FIG. 12, any one of (a) the above-described inverse map of a geometry factor, (b) the sensitivity map, and (c) the distance map based on distance from the magnetic field center may be solely used as a reliability map. Additionally, each of the inverse map of a geometry factor, the sensitivity map, and the distance map may be subjected to predetermined processing such as multiplying a predetermined coefficient, adding or subtracting a predetermined offset value so as to determine a reliability map. Additionally or alternatively, a reliability map may be determined by combining these three types of map.

Moreover, a reliability map may be determined by combining any two of the inverse map of a geometry factor, the sensitivity map, and the distance map the inverse map of geometry factors, e.g., by multiplying the inverse map of a geometry factor by the distance map. As another embodiment, a reliability map may be determined by combining all of the inverse map of a geometry factor, the sensitivity map, and the distance map.

Furthermore, when an SNR or signal intensity of each pixel of an original MRI image is influenced by its imaging conditions except a geometry factor, sensitivity of each of the coil elements 200 and the RF coils 20, and a distance from the magnetic field center, its reliability map may be corrected by using information indicating SNR distribution and/or signal intensity distribution according to those imaging conditions. For example, when data of images are time-sequentially inputted and signal intensity of each pixel of each of these images changes depending on time and space (i.e., signal intensity is indicated by S (x, y, z, t), where "t" indicates elapsed time from a reference time instance), a reliability map W (x, y, z) of each of those images may be corrected by using the signal intensity S (x, y, z, t). Such correction is effective for a case of imaging an anatomical part such as a heart where signal intensity changes according to time phase.

Additionally, the number of a reliability map to be used for generating one quantitative susceptibility image is not limited to one, but plural, e.g., two reliability maps may be used for generating one quantitative susceptibility image. For example, the first reliability map $W_0$ resulting from data having influence on signal intensity and the second reliability map $W_1$ resulting from data having no influence on signal intensity may be generated in advance so as to calculate magnetic susceptibility $\chi$ by solving the formula (6).

(Third Modification of First Embodiment)

Although a reliability map is assumed to be used for calculating a quantitative susceptibility image from a tissue phase image in the first embodiment (the step ST111 in FIG. 4 and the formula (6)), a reliability map may also be used for the phase-wrapping removal processing (in the step ST109 in FIG. 4) and/or the background field removal processing (in the step ST110 in FIG. 4).

For example, the phase-wrapping removal processing under the region-growing method is processing of connecting pixels adjacent to each other by adding or subtracting $2\pi$ when a phase jump occurs in pixels adjacent to the reference point of starting the region-growing method each other. Thus, firstly, by using a reliability map, a pixel whose pixel value is reliable can be detected. Then, by using the detected pixel as the reference point of the region-growing method, the phase-wrapping removal processing can be performed with high accuracy.

Meanwhile, as described above, the RESHARP method is known as one of techniques of the background field removal processing. The RESHARP method generates a local field map derived from body tissues by treating continuity of the local field map as a regularization term in the SHARP method, which utilizes the fact that phase components influenced by a background magnetic field can be expressed by spherical surface harmonics. A local field map derived from body tissues can be generated with high degree of accuracy, by performing weighting based on a reliability map on the optimization processing of the RESHARP method disclosed in the paragraphs below the formula [10] in the Document 3.

Specifically, a local field map $\delta_t$, i.e., a tissue phase image, in which influence of a background magnetic field is removed, can be generated by solving the objective function indicated by the formula (9) as follows.

$$\delta_t = \mathrm{argmin}_{\delta_t} \|W\acute{M}(\nabla^2(\delta-\delta_t))\|_2 + \lambda\|\delta_t\|_2 \qquad \text{Formula (9)}$$

In the formula (9), $\acute{M}$ is a mask indicating a one-size smaller region of the body tissue region and W is a weighting coefficient based on the reliability map.

Further, a PDF method, which estimates a background magnetic field by utilizing the fact that a background magnetic field of an air region is orthogonal to a magnetic field in body tissues, is known as another technique of the background field removal processing.

In the PDF method, the background magnetic field $\delta_b$ can also be estimated on the basis of a reliability map. Specifically, the following formula (10) is given by substituting the reliability map W in the present embodiment for "w" in the formula [11] in the Document 3.

$$\chi_b = \mathrm{argmin}_{\chi_b} \|W\cdot(\delta-d^*\chi_b)\|_2 \qquad \text{Formula (10)}$$

Further, the local field map $\delta_t$ is calculated by the following formulas (11) and (12).

$$\delta_b = d^*\chi_b \qquad \text{Formula (11)}$$

$$\delta_t = \delta - \delta_b \qquad \text{Formula (12)}$$

The local field map $\delta_t$ determined by the formula (12) is a tissue phase image from which influence of a background magnetic field is removed.

As described above, influence of a background magnetic field can be removed by weighted optimization processing based on a reliability map.

(Second Embodiment)

Figure 13:
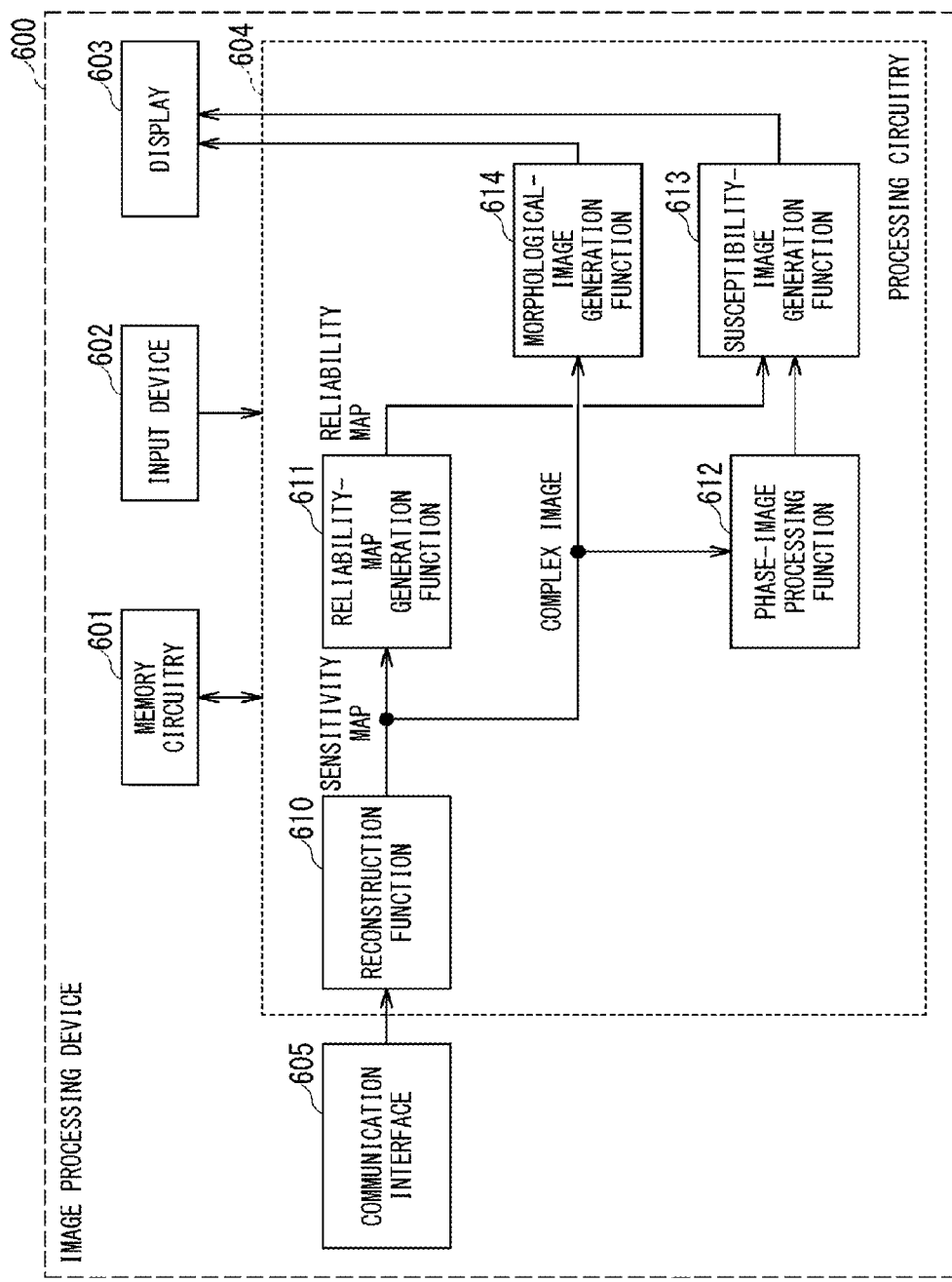
FIG. 13 is a functional block diagram illustrating configuration of an image processing apparatus according to the second embodiment.

FIG. 13 is a block diagram illustrating configuration of the image processing apparatus 600 in the second embodiment. Images generated by an MRI apparatus are inputted to the image processing apparatus 600. The image processing apparatus 600 generates a quantitative susceptibility image from the inputted images. The image processing apparatus 600 may be installed in the same facility as the MRI apparatus from which original images are outputted or may be installed in a facility separated from the facility including the MRI apparatus from which original images are outputted.

The image processing apparatus 600 includes memory circuitry 601, an input device 602, a display 603, processing circuitry 604, and a communication interface 605.

The processing circuitry 604 implements each of a data acquisition function 610, a reliability-map generation function 611, a phase-image processing function 612, a susceptibility-image generation function 613, and a morphological-image generation function 614 by executing a predetermined program stored in the memory circuitry 601.

Out of the above-described components of the image processing apparatus 600, the memory circuitry 601, the input device 602, the display 603, and the processing circuitry 604 are substantially the same as the memory circuitry 41, the input device 43, the display 42, and the processing circuitry 40 of the MRI apparatus 1 in the first embodiment, respectively. Thus, duplicate description on the above-described components is omitted.

Out of the above-described functions of the image processing apparatus 600, the reliability-map generation function 611, the phase-image processing function 612, the susceptibility-image generation function 613, the morphological-image generation function 614 are substantially the same as the reliability-map generation function 403, the phase-image processing function 405, the susceptibility-image generation function 406, and the morphological-image generation function 404 in the first embodiment, and duplicate description is omitted.

The memory circuitry 601 of the image processing apparatus 600 stores MRI images (complex images) imaged and reconstructed by an MRI apparatus which is a source of supplying images. These MRI images are supplied to the image processing apparatus 600 via, for example, a recording medium such as an optical disc. Additionally or alternatively, when the MRI apparatus and the image processing apparatus 600 are connected with each other in a network, the image processing apparatus 600 may acquire MRI images from the network via the communication interface 605.

MRI images to be acquired are, for example, data based on DICOM standards and include various imaging conditions as accompanying information of each image. In formation on the magnetic field center is included in those imaging conditions. Additionally, when an MRI apparatus generates sensitivity maps, the MRI apparatus may add the information on the sensitivity maps to accompanying information of each MRI image. Moreover, a geometry factor calculated from sensitivity maps may be included in accompanying information of each MRI image.

Incidentally, the entirety of the memory circuitry 601, the input device 602, and the communication interface 605 is an example of the acquisition circuit recited in the claims.

Additionally, the RF coils 20 are examples of the receiving coils recited in the claims.

When the processing circuitry 604 receives a command to generate a quantitative susceptibility image from an operator via the input device 602, the processing circuitry 604 acquires an MRI image (complex image) and its accompanying information from the memory circuitry 601 by its data acquisition function 610. Then, when information on sensitivity maps and/or a geometry factor is included in the acquired accompanying information, the processing circuitry 604 generates a reliability map based on the sensitivity maps and/or the geometry factor in a manner similar to the first embodiment. On the other hand, when information on a sensitivity map or a geometry factor is not included in the acquired accompanying information, the processing circuitry 604 generates a reliability map from information on the magnetic field center included in the acquired accompanying information. The processing after this generation of a reliability map is the same as the first embodiment except that the main scan (i.e., the steps ST104 and ST105 in FIG. 4) and reconstruction processing (i.e., the step ST106 in FIG. 4) are not included.

According to the image processing apparatus 600 of the second embodiment, a quantitative susceptibility image can be generated at a place separated from an MRI apparatus which generates the original MRI image from which the quantitative susceptibility image is generated. Additionally, after acquisition of an MRI image, calculation of a quantitative susceptibility image can be performed at a desired time.

According to at least one of the above-described embodiments, a quantitative susceptibility image with high estimation accuracy can be generated.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An MRI apparatus, comprising:
at least one receiving coil configured to receive magnetic resonance signals from an object; and
processing circuitry configured to
generate an image based on the received magnetic resonance signals,
calculate a weighting map of the image based on at least one of a sensitivity characteristic of the at least one receiving coil and a distance from a magnetic field center, and
generate a quantitative susceptibility image, which quantitatively indicates magnetic susceptibility inside a body, from the image by using the calculated weighting map,
wherein the processing circuitry is further configured to generate the quantitative susceptibility image from a phase image indicative of phase information of the image, by performing weighted optimization processing based on the weighting map.

2. The MRI apparatus according to claim 1,
wherein the processing circuitry is further configured to calculate the weighting map in such a manner that the weighting map has a larger value at a position where the sensitivity of the at least one receiving coil is higher.

3. The MRI apparatus according to claim 1,
wherein the processing circuitry is further configured to calculate the weighting map in such a manner that the weighting map has a larger value at a position with a higher signal to noise ratio.

4. The MM apparatus according to claim 1,
wherein the at least one receiving coil comprises a plurality of receiving coils; and
the processing circuitry is further configured to calculate the weighting map by using a sensitivity characteristic of each of the plurality of receiving coils.

5. The MRI apparatus according to claim 1,
wherein the at least one receiving coil comprises a plurality of receiving coils; and
the processing circuitry is further configured to calculate the weighting map based on a geometry factor calculated from a sensitivity characteristic of each of the plurality of receiving coils.

6. The MRI apparatus according to claim 5,
wherein the processing circuitry is further configured to calculate the weighting map by using an inverse of the geometry factor.

7. The MRI apparatus according to claim 1,
wherein the processing circuitry is further configured to calculate the weighting map by combining a sensitivity map and a distance map, the sensitivity map being calculated from the sensitivity characteristic of the at least one receiving coil, and the distance map being calculated from the distance from the magnetic field center.

8. The MM apparatus according to claim 1,
wherein the at least one receiving coil comprises a plurality of receiving coils; and
the processing circuitry is further configured to
calculate a geometry factor based on a sensitivity characteristic of each of the plurality of receiving coils, and
calculate the weighting map by combining any two or all of a map of an inverse of the geometry factor, a sensitivity map, and a distance map, the sensitivity map being calculated from the sensitivity characteristic of each of the plurality of receiving coils, and the distance map being calculated from the distance from a magnetic field center.

9. The MRI apparatus according to claim 1,
wherein the processing circuitry is further configured to correct the weighting map based on an imaging condition excluding the sensitivity characteristic of the at least one receiving coil and the distance from the magnetic field center.

10. The MRI apparatus according to claim 1,
wherein the processing circuitry is further configured to correct the weighting map based on changing signal intensity of the image, when signal intensity of the image changes depending on at least one of space and time.

11. The IVIRI apparatus according to claim 1,
wherein the weighted optimization processing performed by the processing circuitry is processing of minimizing an objective function which includes a data term and a regularization term, by applying the weighting map to the data term.

12. The MRI apparatus according to claim 1,
wherein the weighted optimization processing performed by the processing circuitry is processing of minimizing an objective function which includes a data term and a regularization term, by applying the weighting map to at least one of the data term and the regularization term.

13. The MRI apparatus according to claim 1,
wherein the processing circuitry is further configured to
calculate a phase component attributable to a body tissue from a phase image indicative of phase information of the image, by removing influence of a background magnetic field, and generate the quantitative susceptibility image from the phase component attributable to the body tissue.

14. An image processing apparatus configured to generate a quantitative susceptibility image from an image generated by an MRI apparatus, the image processing apparatus comprising:
an acquisition circuit configured to acquire the image; and
processing circuitry configured to
generate the quantitative susceptibility image, which quantitatively indicates magnetic susceptibility inside a body from the image, by using a weighting map calculated based on at least one of a sensitivity characteristic of a receiving coil used for imaging the image by the MRI apparatus and a distance from a magnetic field center of the MRI apparatus,
wherein the processing circuitry is further configured to generate the quantitative susceptibility image from a phase image indicative of phase information of the image, by performing weighted optimization processing based on the weighting map.

15. The image processing apparatus according to claim 14,
wherein the processing circuitry is further configured to add the weighting map to data of the image as accompanying information thereof.

16. The image processing apparatus according to claim 14,
wherein the processing circuitry is further configured to add the sensitivity characteristic of the receiving coil to data of the image as accompanying information thereof; and
the processing circuitry is further configured to calculate the weighting map by using the sensitivity characteristic of the receiving coil.

17. The image processing device according to claim 14,
wherein the processing circuitry is further configured to add information on the distance from a magnetic field center to data of the image as accompanying information thereof; and
the processing circuitry is further configured to calculate the weighting map by using the information on the distance from the magnetic field center.

18. An image processing method, comprising:
acquiring an image generated by an MRI apparatus; and
generating a quantitative susceptibility image, which quantitatively indicates magnetic susceptibility inside a body from the image, by using a weighting map calculated based on at least one of a sensitivity characteristic of a receiving coil used for imaging the image by the MRI apparatus and a distance from a magnetic field center of the MRI apparatus,
wherein the generating step further includes generating the quantitative susceptibility image from a phase image indicative of phase information of the image, by performing weighted optimization processing based on the weighting map.

19. The image processing method according to claim 18, further comprising calculating the weighting map based on a geometry factor calculated from sensitivity characteristics of a plurality of receiving coils of the MRI apparatus.

* * * * *